United States Patent [19]
Styczynski et al.

[11] Patent Number: 6,060,471
[45] Date of Patent: May 9, 2000

[54] REDUCTION OF HAIR GROWTH

[76] Inventors: Peter Styczynski, P.O. Box 387, Mt. Airy, Md. 21771; Gurpreet S. Ahluwalia, 8632 Stableview Ct., Gaithersburg, Md. 20882; Douglas Shander, 16112 Howard Landing Dr., Gaithersburg, Md. 20878

[21] Appl. No.: 09/010,227

[22] Filed: Jan. 21, 1998

[51] Int. Cl.$^7$ .......................... A61K 31/50; A61K 31/495
[52] U.S. Cl. .......................... 514/248; 514/334; 514/345; 514/634; 514/635; 514/673
[58] Field of Search ................................. 514/248, 334, 514/345, 634, 635, 673

[56] References Cited

U.S. PATENT DOCUMENTS

| | | | |
|---|---|---|---|
| 3,426,137 | 2/1969 | Philpitt et al. | 424/330 |
| 4,039,669 | 8/1977 | Beylar et al. | 424/324 |
| 4,139,638 | 2/1979 | Neri et al. | 424/324 |
| 4,161,540 | 7/1979 | Neri et al. | 424/324 |
| 4,191,775 | 3/1980 | Glen | 424/304 |
| 4,269,831 | 5/1981 | Ferrari et al. | 624/304 |
| 4,370,315 | 1/1983 | Greff et al. | 424/260 |
| 4,439,432 | 3/1984 | Peat | 424/260 |
| 4,508,714 | 4/1985 | Cecic et al. | 424/195.1 |
| 4,517,175 | 5/1985 | Iwabuchi et al. | 424/70 |
| 4,720,489 | 1/1988 | Shander | 514/171 |
| 4,885,289 | 12/1989 | Breur et al. | 514/170 |
| 4,935,231 | 6/1990 | Pigiet | 424/71 |
| 5,095,007 | 3/1992 | Ahluwalia | 514/23 |
| 5,096,911 | 3/1992 | Ahluwalia et al. | 514/212 |
| 5,132,293 | 7/1992 | Shander et al. | 514/665 |
| 5,143,925 | 9/1992 | Shander et al. | 514/378 |
| 5,189,212 | 2/1993 | Ruenitz | 562/468 |
| 5,271,942 | 12/1993 | Haverhagen | 424/451 |
| 5,300,284 | 4/1994 | Wiechers et al. | 424/70 |
| 5,364,885 | 11/1994 | Ahluwalia et al. | 514/563 |
| 5,411,991 | 5/1995 | Shander et al. | 514/665 |
| 5,455,234 | 10/1995 | Ahluwalia et al. | 514/212 |
| 5,474,763 | 12/1995 | Shander et al. | 514/665 |
| 5,648,394 | 7/1997 | Boxall et al. | 514/564 |
| 5,885,982 | 3/1999 | Dolynchuk et al. | 514/210 |

FOREIGN PATENT DOCUMENTS

| | | |
|---|---|---|
| 0 413 528 A1 | 2/1991 | European Pat. Off. . |
| 0 532 210 A2 | 3/1993 | European Pat. Off. . |
| 1 458 349 | 12/1976 | United Kingdom . |
| WO 94/15596 | 7/1994 | WIPO . |
| WO 96/22021 | 7/1996 | WIPO . |
| WO 96/23490 | 8/1996 | WIPO . |
| WO 98/10766 | 3/1998 | WIPO . |

OTHER PUBLICATIONS

H.L. Cooper, "Indentification of the hypusine–containing protein HY+ as translation initiation factor eIF–4D" Proc. Natl. Acad. Sci. USA, vol. 80, pp. 1854–1857, 1983.

Sakurai et al., Pharmalogical study of 6–cyclohexyl–1–hydroxy–4–methyl–2(1H)–pyridone ethanolamine salt, Chemical Abstracts, vol. 83, No. 7, Aug. 18, 1975, Abstract No. 53538.

Fleming et al—"Journal of Cardiovascular Pharmacology" 10 Suppl 10 5149–53 (Abstract), 1987.

Yoshimasa et al—"J. SccJ," 22(3), 165–70 (Japan) (Abstract), 1988.

Bogaert et al—"Journal of International Medical Research" 14(4) 210–6 (U.K.) (Abstract), 1986.

Ransom et al—"Synapse", 5 (4), 294–8 (Abstract), 1990.

Csonga et al., "Evaluation of the metal ion requirement of the human deoxyhypusine hydroxylase from HeLa cells using a novel enzyme assay", FEBS Letters, 380 (1996) 209–214.

Joe et al., "Structural Features of the eIF–5A Precursor Required for Posttranslational Synthesis of Deoxyhypusine", The Journal of Biological Chemistry, vol. 269, No. 41, Oct. 14, 1994, pp. 25916–21.

Jakus et al., "Features of the Spermidine–binding Site in Deoxyhypusine Synthase as Derived from Inhibition Studies", The Journal of Biological Chemistry, vol. 268, No. 18, Jun. 18, 1993, pp. 13154–59.

Andrew G. Messenger, "The Control of Hair Growth: An Overview", The Society for Investigative Dermatology, Inc., 1993.

Park et al., "Hypusine: its post–translational formation in eukaryotic initiation factor 5A and its potential role in cellular regulation", Biofactors, 4:95–104 (1993).

Paz et al., "Hydralazine Inhibition of the Post–Translational Hydroxylation of Deoxyhypusine, A Polyamine–Derived Amino Acid", Biochemical Pharmacology, vol. 33, No. 5, pp. 779–95, 1984.

Adachi et al., "Human Hair Follicles: Metabolism and Control Mechanisms", Journal of the Society of Cosmetic Chemists, 21, 901–924, Dec. 9, 1970.

*Primary Examiner*—Leondard Schenkman
*Attorney, Agent, or Firm*—Fish & Richardson P.C.

[57] ABSTRACT

Mammalian hair growth is reduced by applying to the skin an inhibitor of hypusine biosynthetic pathway.

48 Claims, No Drawings

REDUCTION OF HAIR GROWTH

The invention relates to reducing hair growth in mammals.

A main function of mammalian hair is to provide environmental protection. However, that function has largely been lost in humans, in whom hair is kept or removed from various parts of the body essentially for cosmetic reasons. For example, it is generally preferred to have hair on the scalp but not on the face.

Various procedures have been employed to remove unwanted hair, including shaving, electrolysis, depilatory creams or lotions, waxing, plucking, and therapeutic antiandrogens. These conventional procedures generally have drawbacks associated with them. Shaving, for instance, can cause nicks and cuts, and can leave a perception of an increase in the rate of hair regrowth. Shaving also can leave an undesirable stubble. Electrolysis, on the other hand, can keep a treated area free of hair for prolonged periods of time, but can be expensive, painful, and sometimes leaves scarring. Depilatory creams, though very effective, typically are not recommended for frequent use due to their high irritancy potential. Waxing and plucking can cause pain, discomfort, and poor removal of short hair. Finally, antiandrogens—which have been used to treat female hirsutism—can have unwanted side effects.

It has previously been disclosed that the rate and character of hair growth can be altered by applying to the skin inhibitors of certain enzymes. These inhibitors include inhibitors of 5-alpha reductase, ornithine decarboxylase, S-adenosylmethionine decarboxylase, gamma-glutamyl transpeptidase, and transglutaminase. See, for example, Breuer et al., U.S. Pat. No. 4,885,289; Shander, U.S. Pat. No. 4,720,489; Ahluwalia, U.S. Pat. No. 5,095,007; Ahluwalia et al., U.S. Pat. No. 5,096,911; Shander et al., U.S. Pat. No. 5,132,293; and Shander et al., U.S. Pat. No. 5,143,925.

Hypusine ($N^{68}$-(4-amino-2 (R)-hydroxybutyl) lysine) is a unique amino acid in that it is formed on a synthesized protein by the process called posttranslational modification. Hypusine is only known to occur in a single protein, eukaryotic translation initiation factor 5A (eIF-5A). The formation of hypusine occurs by two distinct steps involving modification of a single lysyl amino acid residue on the eIF-5A protein. The two enzymes which catalyze this reaction are deoxyhypusine synthetase and deoxyhypusine hydroxylase; the biochemical pathway is described below:

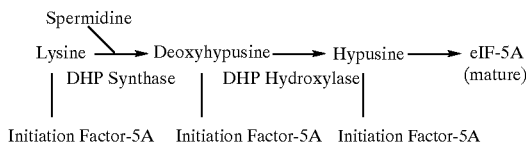

Deoxyhypusine (DHP) synthetase catalyzes the transfer of a 4-aminobutyl moiety from a polyamine, spermidine, to an ε-amino group of a specific lysyl residue on the eIF-5A precursor (amino acid position So for the human eIF-5A). This results in the formation an intermediate, deoxyhypusine. DHP hydroxylase then facilitates a stereospecific hydroxylation of carbon 9 of the intermediate to form hypusine and, hence, a mature or active eIF-5A protein.

The above pathway will be referred to herein as the "hypusine biosynthetic pathway." DHP synthetase and DHP hydroxylase will be referred to collectively as the "hypusine biosynthetic enzymes."

It has now been found that unwanted mammalian (including human) hair growth—particularly androgen-stimulated hair growth—can be reduced by applying to the skin a composition including an inhibitor of the hypusine biosynthetic pathway in an amount effective to reduce hair growth. The unwanted hair growth which is reduced may be normal hair growth, or hair growth that results from an abnormal or diseased condition.

The hypusine biosynthetic pathway can be inhibited in a number of ways. Preferably, an inhibitor of a hypusine biosynthetic enzyme is used to inhibit the enzyme and thus the pathway.

Inhibitors of hypusine biosynthetic enzymes are known. See, for example, J. Jakus et al., J. Biological Chemistry 268:13151–13159, 1993; R. Csonga et al., FEBS Letters 380:209–214, 1996; and Paz et al., Biochem. Pharmacol. 33:779–785, 1984.

DHP synthase inhibitors include 1,3-diaminopropane; 1,6-diaminohexane; 1,7-diaminoheptane; 1,8-diaminooctane; 1,9-diaminononane; caldine; cadaverine; N-(3-amino-propyl)cadaverine; $N^4$-benzyl-spermidine; 1-methylspermidine; 6-fluorospermidine; 6,6-difluorospermidine; guazatine ($N^1,N^{16}$-bisguanyl-2 (1,8-diaminooctane)); $N^1,N^6$-bisguanyl-1,6-diaminohexane; $N^1,N^7$ bisguanyl-1,7-diaminoheptane; $N^1$, $N^8$-bisguanyl-1,8-diaminooctane; $N^1$-guanyl-1,7-diaminoheptane; $N^1$-guanyl-1,8-diaminooctane; $N^1$-guanyl caldine; $N^1,N^7$-bisguanyl caldine; $N^1$-guanyl spermidine; $N^8$-guanyl spermidine; and hirudonin ($N^1,N^8$-bisguanyl spermidine).

DHP hydroxylase inhibitors include ciclopiroxolamine; ciclopirox; rilopirox; piroctone; α,α'-dipyridyl; metipirox; 4,6-diphenyl-1-hydroxypyridine-2-one and hydralazine.

The inhibitor preferably is incorporated in a topical composition which includes a non-toxic dermatologically acceptable vehicle or carrier which is adapted to be spread upon the skin. Examples of suitable vehicles are acetone, alcohols, or a cream, lotion, or gel which can effectively deliver the active compound. One vehicle is disclosed in U.S. Pat. No. 5,648,394. In addition, a penetration enhancer may be added to the vehicle to further enhance the effectiveness of the formulation.

The concentration of the inhibitor in the composition may be varied over a wide range up to a saturated solution, preferably from 0.1% to 30% by weight or even more; the reduction of hair growth increases as the amount of inhibitor applied increases per unit area of skin. The maximum amount effectively applied is limited only by the rate at which the inhibitor penetrates the skin. The effective amounts may range, for example, from 10 to 3000 micrograms or more per square centimeter of skin.

The composition should be topically applied to a selected area of the body from which it is desired to reduce hair growth. For example, the composition can be applied to the face, particularly to the beard area of the face, i.e., the cheek, neck, upper lip, and chin. The composition can also be applied to the legs, arms, torso or armpits. The composition is particularly suitable for reducing the growth of unwanted hair in women suffering from hirsutism or other conditions. In humans, the composition should be applied once or twice a day, or even more frequently, for at least three months to achieve a perceived reduction in hair growth. Reduction in hair growth is demonstrated when the frequency of hair removal is reduced, or the subject perceives less hair on the treated site, or quantitatively, when the weight of hair removed by shaving (i.e., hair mass) is reduced.

Male intact Golden Syrian hamsters are considered acceptable models for human beard hair growth in that they display oval shaped flank organs, one on each side, each about 8 mm. in major diameter, which grow thick black and coarse hair similar to human beard hair. These organs produce hair in response to androgens in the hamster. To evaluate the effectiveness of a composition including an inhibitor of the hypusine biosynthetic pathway, the flank organs of each of a group of hamsters are depilated by applying a thioglycolate based chemical depilatory (Surgex) and/or shaved. To one organ of each animal 10 μl. of vehicle alone once a day is applied, while to the other organ of each animal an equal amount of vehicle containing an inhibitor of the hypusine biosynthetic pathway is applied. After thirteen applications (one application per day for five days a week), the flank organs are shaved and the amount of recovered hair (hair mass) from each is weighed. Percent-reduction of hair growth is calculated by subtracting the hair mass (mg) value of the test compound treated side from the hair mass value of the vehicle treated side; the delta value obtained is then divided by the hair mass value of the vehicle treated side, and the resultant number is multiplied by 100.

The above-described assay will be referred to herein as the "Golden Syrian hamster" assay. Preferred compositions provide a reduction in hair growth of at least about 15%, more preferably at least about 40%, and most preferably at least about 60% when tested in the Golden Syrian hamster assay. A number of inhibitors of the hypusine biosynthetic pathway were tested in the Golden Syrian hamster assay; the results are provided in Table 1:

TABLE I

Inhibition of Hair Mass by Inhibitors of Deoxyhypusine Synthetase

|  |  |  |  | Hair Mass (mg) | |
| --- | --- | --- | --- | --- | --- |
| Compound | Dose | pH | % Inhibition | Treated | Vehicle Control |
| 1,8-Diaminooctane | 10% | 8.0 | 74 ± 6 | 0.70 ± .12 | 2.76 ± .30 |
| 1,7-Diaminoheptane | 10% | 7.5 | 67 ± 4 | 0.80 ± .11 | 2.46 ± .16 |
| $N^4$-Benzylspermidine | 10% | 8.5 | 62 ± 4 | 1.05 ± .12 | 2.74 ± .12 |
| 1,6-Diaminohexane | 10% | 8.0 | 51 ± 5 | 1.50 ± .20 | 3.15 ± .45 |
| 1,9-Diaminononane | 10% | 7.6 | 50 ± 13 | 1.27 ± .56 | 2.91 ± 1.3 |
| Cadaverine | 10% | 6.0 | 43 ± 4 | 1.91 ± .15 | 3.43 ± .22 |

All compounds were administered in a vehicle containing water (68%), ethanol (16%), propylene glycol (5%), dipropylene glycol (5%), benzyl alcohol (4%), and propylene carbonate (2%). This vehicle also was used in the testing described below.

Dose-dependent inhibition of hair mass was shown for the enzyme inhibitor 1,8-diaminooctane (Table II, below). An effective reduction in hair mass was also obtained by the two deoxyhypusine hydroxylase inhibitors ciclopiroxolamine (44% reduction) and hydralazine (33% reduction) (Table III, below).

TABLE II

Dose-Dependent Inhibition of Hair Mass by 1,8-Diaminooctane

|  |  |  | Hair Mass (mg) | |
| --- | --- | --- | --- | --- |
| 1,8-Diaminooctane | pH | % Inhibition | Treated | Vehicle Control |
| 2% | 9.0 | 24 ± 8 | 1.88 ± .25 | 2.47 ± .20 |
| 5% | 9.0 | 48 ± 10 | 1.86 ± .37 | 3.71 ± .26 |
| 10% | 8.0 | 74 ± 6 | 0.70 ± .12 | 2.76 ± .30 |

TABLE III

Inhibition of Hair Mass by Inhibitors of Deoxyhypusine Hydroxylase

|  |  |  |  | Hair Mass (mg) | |
| --- | --- | --- | --- | --- | --- |
| Compound | Dose | pH | % Inhibition | Treated | Vehicle Control |
| Ciclopiroxolamine | 10% | 9.0 | 44 ± 17 | 0.92 ± .21 | 1.81 ± .25 |
| Hydralazine | 5% | 5.0 | 33 ± 7 | 1.38 ± .14 | 2.12 ± .16 |

Testing also was conducted that demonstrates that inhibitors of the hypusine biosynthetic pathway reduced the incorporation of $^3$H-spermidine into 18 kD human hair follicle protein.

Human hair follicles derived from face lift procedures were isolated and placed in Williams E medium containing antibiotics, glutamine, insulin and hydrocortisone. Follicles were cultured for 48 hours at 37° C. in the presence of 1,6-diaminohexane (0.2 mM), 1,8-diaminooctane (0.2 mM), ciclopiroxolamine (0.2 mM) or hydralazine (0.2 mM). Control follicles were maintained in Williams E without any inhibitors present. At the end of the 48 hour period, $^3$H-spermidine (1 μCi/mmol) was added to the culture for 6 hours. The hair follicles were washed in phosphate buffered saline to remove nonincorporated $^3$H-spermidine, and the follicles were homogenized in a buffer, pH 7.4, containing Tris (50 mM) and sucrose (0.5 mM). Hair follicle protein was applied to a 10% polyacrylamide gel. After the proteins were separated on the gel using a constant voltage (125 V), they were stained with coomassie blue. Bands were visualized in the 18 kD area corresponding to the eIF-5A protein. The protein bands were cutout of the gel and solubilized with BTS-450 (Beckman). The liquid scintillation fluid Econoscint (12 mL) was added to each sample, which was analyzed for $^3$H-spermidine incorporation by scintillation spectrometry. Inhibitors of deoxyhypusine synthase (1,6-diaminohexane and 1,8-diaminooctane) and of deoxyhypusine hydroxylase (ciclopiroxolamine and hydralazine) strongly inhibited (47–100%) the incorporation of radiolabeled spermidine into hair follicle protein(s) in the region of 18 kD; the results are presented in Table IV.

TABLE IV

Incorporation of $^3$H-Spermidine into 18 kD Human Hair Follicle Proteins

| Target Enzyme | Inhibitor | Incorporation (pmol/mg protein) | % Reduction |
| --- | --- | --- | --- |
| Control | None | 19.6 | 0 |
| Deoxyhypusine Synthase | 1,6-Diaminohexane | <1.0 | 100 |
|  | 1,8-Diaminooctane | <1.0 | 100 |
| Deoxyhypusine Hydroxylase | Ciclopiroxolamine | <1.0 | 100 |
|  | Hydralazine | 10.3 | 47 |

Other embodiments are within the claims.

What is claimed is:

1. A method of reducing mammalian hair growth which comprises
   selecting an area of skin from which reduced hair growth is desired; and
   applying to said area of skin a dermatologically acceptable composition comprising an inhibitor of the hypusine biosynthetic pathway in an amount effective to reduce hair growth.

2. The method of claim 1, wherein said inhibitor inhibits a hypusine biosynthetic enzyme.

3. The method of claim 2, wherein said enzyme comprises deoxyhypusine synthase.

4. The method of claim 2, wherein said enzyme comprises deoxyhypusine hydroxylase.

5. The method of claim 1, wherein said inhibitor inhibits the maturation or activation of eIF-5A.

6. The method of claim 1, wherein said inhibitor comprises 1,3-diaminopropane.

7. The method of claim 1, wherein said inhibitor comprises 1,6-diaminohexane.

8. The method of claim 1, wherein said inhibitor comprises 1,7-diaminoheptane.

9. The method of claim 1, wherein said inhibitor comprises 1,8-diaminooctane.

10. The method of claim 1, wherein said inhibitor comprises 1,9-diaminononane.

11. The method of claim 1, wherein said inhibitor comprises caldine.

12. The method of claim 1, wherein said inhibitor comprises cadaverine.

13. The method of claim 1, wherein said inhibitor comprises N-(3-amino-propyl)cadaverine.

14. The method of claim 1, wherein said inhibitor comprises $N^4$-benzyl-spermidine.

15. The method of claim 1, wherein said inhibitor comprises 1-methylspermidine.

16. The method of claim 1, wherein said inhibitor comprises 6-fluorospermidine.

17. The method of claim 1, wherein said inhibitor comprises 6,6-difluorospermidine.

18. The method of claim 1, wherein said inhibitor comprises $N^1,N^{16}$-bisguanyl-2(1,8-diaminooctane).

19. The method of claim 1, wherein said inhibitor comprises $N^1,N^6$-bisguanyl-1,6-diaminohexane.

20. The method of claim 1, wherein said inhibitor comprises $N^1,N^7$-bisguanyl-1,7-diaminoheptane.

21. The method of claim 1, wherein said inhibitor comprises $N^1,N^8$-bisguanyl-1,8-diaminooctane.

22. The method of claim 1, wherein said inhibitor comprises $N^1$-guanyl-1,7-diaminoheptane.

23. The method of claim 1, wherein said inhibitor comprises $N^1$-guanyl-1,8-diaminooctane.

24. The method of claim 1, wherein said inhibitor comprises $N^1$-guanyl caldine.

25. The method of claim 1, wherein said inhibitor comprises $N^1,N^7$-bisguanyl caldine.

26. The method of claim 1, wherein said inhibitor comprises $N^1$-guanyl spermidine.

27. The method of claim 1, wherein said inhibitor comprises $N^8$-guanyl spermidine.

28. The method of claim 1, wherein said inhibitor comprises hirudonin.

29. The method of claim 1, wherein said inhibitor comprises ciclopiroxolamine.

30. The method of claim 1, wherein said inhibitor comprises ciclopirox.

31. The method of claim 1, wherein said inhibitor comprises rilopirox.

32. The method of claim 1, wherein said inhibitor comprises piroctone.

33. The method of claim 1, wherein said inhibitor comprises $\alpha,\alpha'$-dipyridyl.

34. The method of claim 1, wherein said inhibitor comprises metipirox.

35. The method of claim 1, wherein said inhibitor comprises 4,6-diphenyl-1-hydroxypyridine-2-one.

36. The method of claim 1, wherein said inhibitor comprises hydralazine.

37. The method of claim 1, wherein the concentration of said inhibitor of in said composition is between 0.1% and 30% by weight.

38. The method of claim 1, wherein the composition provides a reduction in hair growth of at least 40% when tested in the Golden Syrian hamster assay.

39. The method of claim 1, wherein the composition provides a reduction in hair growth of at least 60% when tested in the Golden Syrian hamster assay.

40. The method of claim 1, wherein the inhibitor is applied to the skin in an amount of from 10 to 3000 micrograms of said inhibitor per square centimeter of skin.

41. The method of claim 1, wherein said mammal is a human.

42. The method of claim 41, wherein said area of skin is on the face of the human.

43. The method of claim 41, wherein said area of skin is on a leg of the human.

44. The method of claim 41, wherein said area of skin is on an arm of the human.

45. The method of claim 41, wherein said area of skin is in an armpit of the human.

46. The method of claim 41, wherein said area of skin in on the torso of the human.

47. The method of claim 41, wherein said human is a woman suffering from hirsutism.

48. The method of claim 1, wherein said hair growth comprises androgen stimulated hair growth.

\* \* \* \* \*

UNITED STATES PATENT AND TRADEMARK OFFICE
CERTIFICATE OF CORRECTION

PATENT NO. : 6,060,471
DATED : May 9, 2000
INVENTOR(S) : Peter Styczynski et al.

It is certified that error appears in the above-identified patent and that said Letters Patent is hereby corrected as shown below:

Title page,

Column 1,
Under Foreign Patent Documents,
Delete "0532210 A2" and insert -- 0532219 A2 --

Column 2,
Under Other Publications,
Jakus et al., delete "in" after Site and insert -- of --

Signed and Sealed this

Sixteenth Day of October, 2001

Attest:

NICHOLAS P. GODICI
Attesting Officer
Acting Director of the United States Patent and Trademark Office